US007927867B2

(12) United States Patent
Khaldoyanidi

(10) Patent No.: US 7,927,867 B2
(45) Date of Patent: Apr. 19, 2011

(54) DEVICE FOR EVALUATING IN VITRO CELL MIGRATION UNDER FLOW CONDITIONS, AND METHODS OF USE THEREOF

(75) Inventor: Sophia K Khaldoyanidi, San Diego, CA (US)

(73) Assignee: Cascade Life Sciences, Inc., San Diego, CA (US)

( * ) Notice: Subject to any disclaimer, the term of this patent is extended or adjusted under 35 U.S.C. 154(b) by 0 days.

(21) Appl. No.: 11/395,812

(22) Filed: Mar. 31, 2006

(65) Prior Publication Data
US 2006/0234207 A1    Oct. 19, 2006

Related U.S. Application Data

(60) Provisional application No. 60/667,591, filed on Mar. 31, 2005.

(51) Int. Cl.
*C12M 1/34* (2006.01)
*C12M 3/00* (2006.01)
*C12M 1/12* (2006.01)

(52) U.S. Cl. ............... 435/288.4; 435/288.3; 435/287.9; 435/288.5; 435/287.8; 435/305.1; 435/305.2; 435/305.3; 435/287.1; 435/297.5; 435/287.3; 422/99

(58) Field of Classification Search ............... 435/287.3, 435/288.3, 288.4, 287.9, 388.5, 287.8, 305.1, 435/305.3, 305.2, 297.1, 297.5; 422/99
See application file for complete search history.

(56) References Cited

U.S. PATENT DOCUMENTS

| 5,190,878 | A  | * | 3/1993  | Wilhelm .................. 435/297.2 |
| 5,460,945 | A  | * | 10/1995 | Springer et al. ............. 435/7.24 |
| 5,599,688 | A  | * | 2/1997  | Grass ........................... 435/29 |
| 6,119,506 | A  | * | 9/2000  | Gibson et al. ................... 73/38 |
| 6,706,520 | B2 | * | 3/2004  | Han et al. .................. 435/287.9 |
| 2003/0215941 | A1 | * | 11/2003 | Campbell et al. ............ 435/325 |
| 2004/0132175 | A1 | * | 7/2004  | Vetillard et al. ........... 435/297.1 |
| 2007/0272000 | A1 | * | 11/2007 | Kahl et al. .................. 73/53.01 |

FOREIGN PATENT DOCUMENTS
EP         0112155 A2 *  6/1984

OTHER PUBLICATIONS

Siminovitch, L., et al.,"The Distribution of Colony-forming Cells Among Spleen Colonies," J Cell Comp Physiol, 1963, 327-336, 62.
Lord, B.I., et al., "On the Late Seeding of CFU-S to the Spleen: 8 vs 12-day CFU-S," Exp. Hematol., 1989, 836-842, 17.
Visser, J.W.M., et al., "In vivo studies on the regeneration kinetics of enriched populations of . . . ," Cell Tissue Kinet., 1983, 385-392, 16.

(Continued)

*Primary Examiner* — Nathan A Bowers
(74) *Attorney, Agent, or Firm* — Lewis Kohn & Fitzwilliam LLP; David M. Kohn

(57) ABSTRACT

The current invention is directed towards a device that useful for studying cell migration. It is preferred that the device is configured to study stem cell, particularly hematopoietic stem/precursor cell homing. The device allows for detailed analysis of the various phases of the multiphase homing process. There are also provided herein, novel methods of using the device, including, but not limited to, dissection of the homing process under microenvironmental conditions mimicking healthy conditions, diseased conditions, inflammatory conditions, drug treatment conditions and experimental conditions.

24 Claims, 10 Drawing Sheets

OTHER PUBLICATIONS

Chiu, Jeng-Jiann, et al., "Shear stress inhibits adhesion molecule expression in vascular . . . ," Blood, 2003, 2667-2674, 101(7).
Nerem, Robert M., "Shear force and its effect on cell structure and function," ASGSB Bulletin, 1991, 87-94, 4(2).
Barakat, Abdul I., "Responsiveness of vascular endothelium to shear stress . . . ," International Journal of Molecular Medicine, 1999, 323-332, 4.
Shyy, John Y-J., "Mechanotransduction in endothelial responses to shear stress . . . ," Biorheology, 2001, 109-117, 38.
Fisher, Aron B., "Endothelial cellular response to altered shear stress," Am J Physiol Lung Cell Mol Physiol, 2001, L529-L533, 281.
Vermeulen, et al., (1998) Blood, 92(3):894-900.
Hendrikx PJ, et al., (1996) Exp Hemat 24:129-140.
Oostendorp, et al., (2000) Bone Marrow Transpl., 26(5):559-566.
Mazo, et al., (1998) J Exp Med 188(3):465-474.
Cinamon, et al., (2001) J Leukoc Biol 69:860-866.
Bautz, et al., (2000) Exp Hematol 28(6):700-706.
Hardy, Minguell, (1993) Scanning Microscopy 7(1):333-341.
Hardy, Megason, (1996) Hematol Oncol 14:17-27.
Wright, et al., (2001) Science 294:1933-1936.
Topper, et al., (1999) Mol Med Today 5(1):40-46.
Nerem, et al., (1998) Am J Med Sci 16(3):169-175.
Ballermann, et al., (1998) Kidney Int Suppl 67:S100-108.
Rainger, et al., (2001) Immunol Methods 255(1-2):73-82.

* cited by examiner

Fig 3B
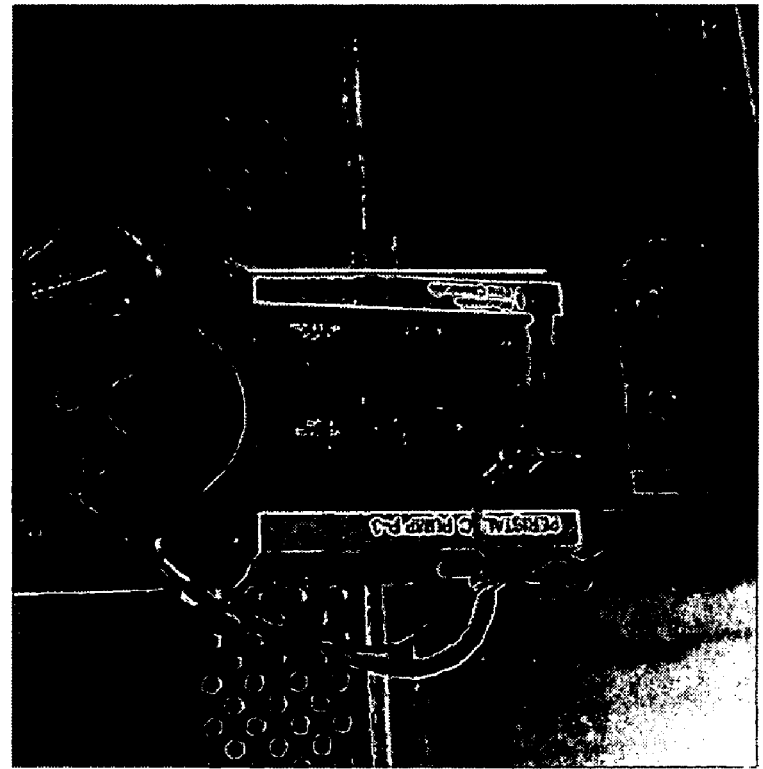
Fig 3A
Figures 3A and 3B

US 7,927,867 B2

DEVICE FOR EVALUATING IN VITRO CELL MIGRATION UNDER FLOW CONDITIONS, AND METHODS OF USE THEREOF

RELATED APPLICATIONS

This application claims the benefit of U.S. provisional patent application Ser. No. 60/667,591, filed Mar. 31, 2005, the entirety of which is hereby incorporated by reference.

FIELD OF THE INVENTION

This invention relates generally to the field of cell migration or homing and provides a device and method for evaluation thereof.

BACKGROUND

Transplantation of hematopoietic stem/progenitor cells (HSPC) is a required procedure for patients who have undergone high-dose chemotherapy and irradiation, and its efficiency depends on the homing ability of the intravenously administered HSPC. Homing of HSPC is a complex process strictly regulated by a multitude of factors.

HSPC trafficking represents one of the most important frontiers in clinical and experimental hematology. Transplantation of HSPC is widely used for the reconstitution of bone marrow hematopoiesis ablated by chemoradiotherapy. Trafficking of HSPC into the bone marrow is a complex and strictly regulated process which is controlled by a number of adhesion molecules, as well as by soluble factors, e.g., chemokines and the extracellular matrix (ECM).

Mature blood cells have a limited life span and have to therefore be constantly replenished by the committed, actively proliferating progenitors. While chemoradiotherapy eliminates dividing cells, including the pool of cycling HSPC, the recovery of mature blood cells following treatment requires a prolonged period of time and is generally accompanied by pancytopenia and bone marrow hypoplasia. Transplantation of HSPC is utilized to recover bone marrow hematopoietic activity after chemoradiotherapy, and its efficiency ultimately depends on the facility of HSPC homing. Homing of HSPC into the bone marrow is regulated by a vast variety of soluble and membrane-bound factors, including adhesion molecules, as well as cytokines, chemokines and interleukins, and ECM. The CD44/HA pathway is but one of the numerous cell signaling pathways mediating HSPC homing.

The generally used method of evaluation of HSPC homing is based on the lethal irradiation of animals followed by an intravenous administration of HSPC. After different periods of time (from 3 hours to 14 days, depending on the experimental design), the bone marrow and peripheral blood cells are harvested and examined for the number of HSPC using various assays (in vitro and in vivo clonogenic assays, FACS). It has been assumed that harvesting of the bone marrow early (3 hours) after the injection allows for the enumeration of "homed" cells (Vermulen M, et al (1998) Blood 92(3):894-900; Siminovich L, et al (1963) J Cell Comp Physiol 62:327; Hendrix P J, et al (1996) Exp Hemat 24:129-140; Oostendorp R A, et al (2000) Bone Marrow Transpl 26(5):559-556). However, because of the anatomical structure of the bone marrow, this technique does not make feasible the distinction of cells that have transmigrated into the extravascular marrow space from cells that have been arrested on the bone marrow vascular endothelium or are still rolling on its surface.

Another method for studying HSPC homing is based on the marrow repopulating ability (MRA) of HSPC injected into lethally irradiated recipients (Lord B I, et al. (1989) Exp Hematol 17:836; Visser J W M, Eliason J F. (1983) Cell Tissue Kinet. 16:385). In this model, bone marrow cells are harvested 2 weeks after bone marrow transplantation and the number of HSPCs is measured in CFU and CFUs assays. The assumption in this assay is that the amount of HSPC progeny directly correlates with the number of homed HSPC. Although this method gives a general understanding as to the involvement of selectively targeted cell surface molecules in the regulation of HSPC homing, it does not discriminate between the different phases of the homing cascade. Furthermore, because of the different turnover of cell surface receptors and the various antigen/antibody dissociation kinetics, effects of antibodies may be masked.

A recently proposed technique for studying HSPC homing is based on intravital microscopy of murine scalp bone marrow circulation (Mazo I, et al. (1998) J Exp Med 188(3):465-474). This technique provides for visualization of endothelial cell interactions under physiological flow conditions. Unfortunately, the technique does not permit long-term observation of these mice. Furthermore, using rodents to study migration of human HSPC may not authentically reflect the actual events in human bone marrow because many of the soluble and cell membrane associated molecules involved in regulating HSPC homing are species specific.

Approaches for studying cell migration also include static assays and assays under flow conditions. The phenotype and functions characteristics of endothelial cells in static conditions differ significantly from those under physiological flow. Static assays (adhesion and transwell assays) do not fairly represent HSPC-endothelial cell interactions occurring in vivo. Physiologic flow assays typically employ flow chambers. The existing flow chambers comprise a single compartment and provide a useful tool for examining tethering and adhesion of cells. However, there is no adequate device or method for studying the chemokine-mediated transmigration of cells under the conditions of flow. Currently, the only technique enumerating the number of migrated cells under the conditions of flow is based on the ability of the adherent cells to crawl beneath the cells that were grown on the glass slide (Cinamon G, et al (2001) J Leukoc Biol 69:860-866). This assay is monitored under the microscope using a high magnification objective, but is limited in that: (a) only a limited number of cells can be analyzed; (b) analysis is non-quantitative; (c) chemokine-mediated migration cannot be studied; (d) the microenvironment effects on endothelial cell function cannot be studied; and (e) there is no means for distinguishing between transmigrated cells and cells arrested in the endothelium.

Finally, none of the existing techniques permit manipulation of the local bone marrow microenvironment, and this limitation of these prior art techniques is crippling research into the role of the microenvironment in the regulation of endothelial cells function, which is becoming increasingly appreciated (Bautz F, et al (2000) Exp Hematol 28(6):700-706.). Although existing techniques have provided a large amount of important information, new methods are now required that will allow for visualizing each step of the homing cascade and for delineating mechanisms mediating HSPC homing: including endothelial cell, HSPC-ECM and HSPC-stromal cell interactions.

SUMMARY OF THE INVENTION

One embodiment of the present invention relates to a device for studying HSPC homing. The device provides a detailed analysis of the multiple phases associated with HSPC homing, thereby allowing the biomolecular dissection of each phase and the cells within that phase.

In one particular aspect of the present invention, there is provided a parallel flow chamber comprised of two compartments. The chamber of the device is divided into an upper compartment and a lower compartment by a membrane. The membrane is preferably porous, thereby allowing for cell transmigration.

A method is also provided for determining which phase of homing a cell is in, for determining the biomolecular makeup of the cell and the environment causing the cell to exist in a particular phase, and for screening of compounds that modulate the cells through the phases of homing.

BRIEF DESCRIPTION OF THE DRAWINGS

FIG. 3A is an illustration of the device in a cell culture hood.

FIG. 3B is an illustration of the device in a call culture incubator.

DETAILED DESCRIPTION OF THE INVENTION

Figure 1A:
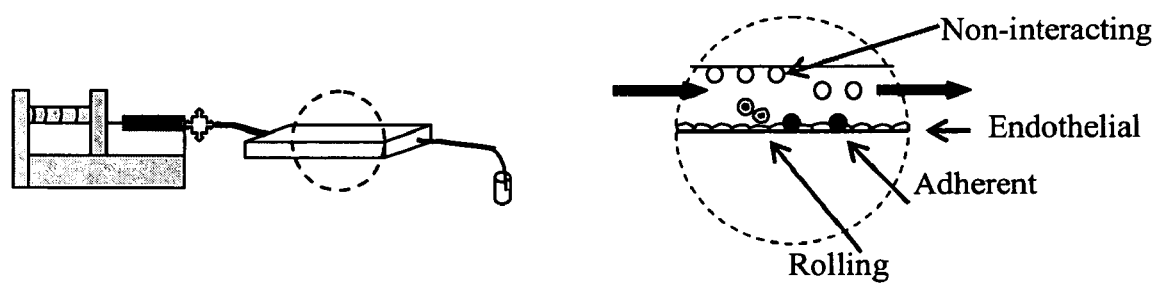
FIG. 1A illustrates the prior art flow chambers having all cells of the homing process in a single compartment.

Since many terms in the area of experimental hematology are not used conventionally, we here define our use of some terminology.

Homing: There are multiple interpretations of this term in the literature. Herein, HSPC homing is defined as the ability of HSPC to find the bone marrow hematopoietic niche, to lodge within it, and to produce progeny (Tavasolli M, Hardy C. (1990) Blood 76(6):1059-1070; Hardy C, Minguell J. (1993) Scanning Microscopy 7(1):333-341; Hardy C, Megason G. (1996) Hematol Oncol 14:17-27). Therefore, homing is divided into two major phases: (1) the extravasation phase; and (2) the seeding of the bone marrow phase. According to this definition, cells arrested on the bone marrow sinusoidal endothelium are not yet considered homed cells. Similarly, an extravasated cell that has not reached an appropriate hematopoietic niche and has not produced progeny under the conditions of physiological demand cannot be regarded as a homed cell.

Extravasation: is the first step in a multi-step phase for HSPC homing. Extravasation involves interaction of HSPC with the bone marrow vascular endothelium under the conditions of physiological flow and includes: (1) tethering of cells (e.g., rolling), (2) adhesion to the luminal surface of endothelial cells, and (3) diapedesis (e.g., transmigration) across the endothelium.

Seeding: The extravasated cell migrates through the bone marrow ECM either using its own enzymatic activities or by inducing such activities in the surrounding cells. The cell then (i) finds a microenvironment that produces the appropriate hematopoiesis-supportive factors and (ii) responds by proliferation and self-renewal.

Marrow Repopulating Ability: It is generally accepted that there exist two phases of bone marrow repopulation. The first phase is mediated by short-term repopulating HSPC and sustains hematopoiesis in a lethally irradiated animal within the first four weeks after transplantation. The second phase involves seeding of more primitive, long-term repopulating HSPC, which contributes to hematopoiesis after a longer period of time.

Hematopoietic microenvironment: refers to a regulatory network comprising soluble and membrane-bound molecules and cells.

Cells of the hematopoietic microenvironment (or bone marrow accessory cells): heterogeneous populations of cells comprising stromal cells, blanket cells, adipocytes, reticular cells, monocytes/macrophages, granulocytes, lymphocytes, and originating from either hematopoetic stem cells (HSC) or mesenchymal stem cells (MSC).

Mesenchymal stem cells (MSC): give rise to at least seven cell types, including, osteocytes, chondrocytes, adipocytes, tenocytes, myotubes, astrocytes and hematopoietic-supportive stroma.

Stromal cells: fibroblast-like cells which originate from MSC and play a crucial role in the regulation of hematopoiesis in the bone marrow.

Existing techniques for studying homing of human HSPC are not ample, thus there is herein disclosed a novel device and method for monitoring each step of human HSPC trafficking under the conditions of physiological flow.

In the preferred embodiment there is provided a parallel flow chamber comprised of two compartments separated by a porous membrane for studying HPSC homing. This device is useful for studying and manipulating peripheral blood and bone marrow cell recovery following chemoradiotherapy and provides a basis for the developing new strategies for stem cell transplantation following total body irradiation.

One problem with the techniques of the prior art is that none of these techniques provide a means for differentiating between cells extravasated into the bone marrow extravascular space, and cells arrested within the bone marrow microvasculature. Thus, there is herein provided a parallel laminar flow chamber comprised of two chambers separated by a porous membrane that allows for parsing out the multiple phases of HSPC homing and further examining conditions relating to tethering, adhesion, diapedesis and seeding. Because the device provided herein is a flow chamber, HSPC homing can be studied under physiological flow conditions. The two-compartment parallel flow chamber provided herein allows for assessment of the influence of hematopoietic microenvironment on HSPC and of the endothelial cell interactions under conditions of shear stress. The device, therefore, provides a basis for understaiding HSPC homing leading to improved therapeutic strategies for HSPC transplantation following chemoradiotherapy.

Recent evidence shows that 92.8% of intravenously administered HSPCs are cleared from the circulation of a recipient mouse within 30 seconds, and 99.6% of HSPC disappeared from circulation within 6 min (Wright D, et al (2001) Science 294:1933-1936). However the rapid disappearance of HSPC from blood does not imply equivalent migration of HSPC across the endothelial layer. Thus, the time of co-culture that is required for chemokine-mediated transmigration of HSPC, as well as optimal shear stress, can be determined using the current device.

The effect of cells surrounding endothelium on the phenotypic characteristic of vascular endothelial cells has been recently described. For example, it has been demonstrated that shear stress conditions induce expression of ICAM-1, VCAM-1 and E-selectin on the surface of endothelial cells if co-cultured with smooth muscle cells (Chiu J J, et al (2003) Blood 101:2667-2674). However, the effect of the hematopoietic microenvironment, including hematopoiesis-supportive stromal cells, on bone marrow sinusoidal endothelium is largely unknown. Cross-talk between bone marrow sinusoidal endothelial cells and cells of hematopoietic microenvironment may affect endothelial cells, the HSPC interactions therewith may, and, resultantly, HSPC homing. The device of the current invention allows for analysis of the combined effects of hematopoietic microenvironment and shear stress on the phenotype of endothelial cells, and in turn provides for examination of the functions of endothelial cells, e.g. their ability to support transmigration of HSPC.

FIG. 1A is a diagram of a typical prior art laminar flow chamber. The chamber consists of a single cell. Endothelial cells grown on a cover slip are placed on the bottom of the cell. Defined levels of flow (wall shear stress) are applied to the cover slip in the flow chamber by perfusing media with a constant infusion syringe pump (Harvard Apparatus), followed by injection of cells over a period of 2 min (right). Injected cells are collected from the outlet catheter after interacting with the endothelial monolayer.

Unlike the device described in FIG. 1A, the device of the present invention allows examination of HSPC transmigration. This ability to investigate the functions of endothelial cells (i.e. their ability to support the transmigration of HSPC) is one of the distinguishing characteristics of the present invention over the prior art. Specifically, the device in FIG. 1A is functionally limited in that HSPC transmigration across the endothelial cells could not be examined due to the single cell nature of the device. The present invention overcomes such limitations so that the entire cascade of events may be examined. Furthermore, the multi-cell nature of the device of the present invention allows environmental manipulation of the chambers, enabling the analysis of several variables at once.

Figure 5A:
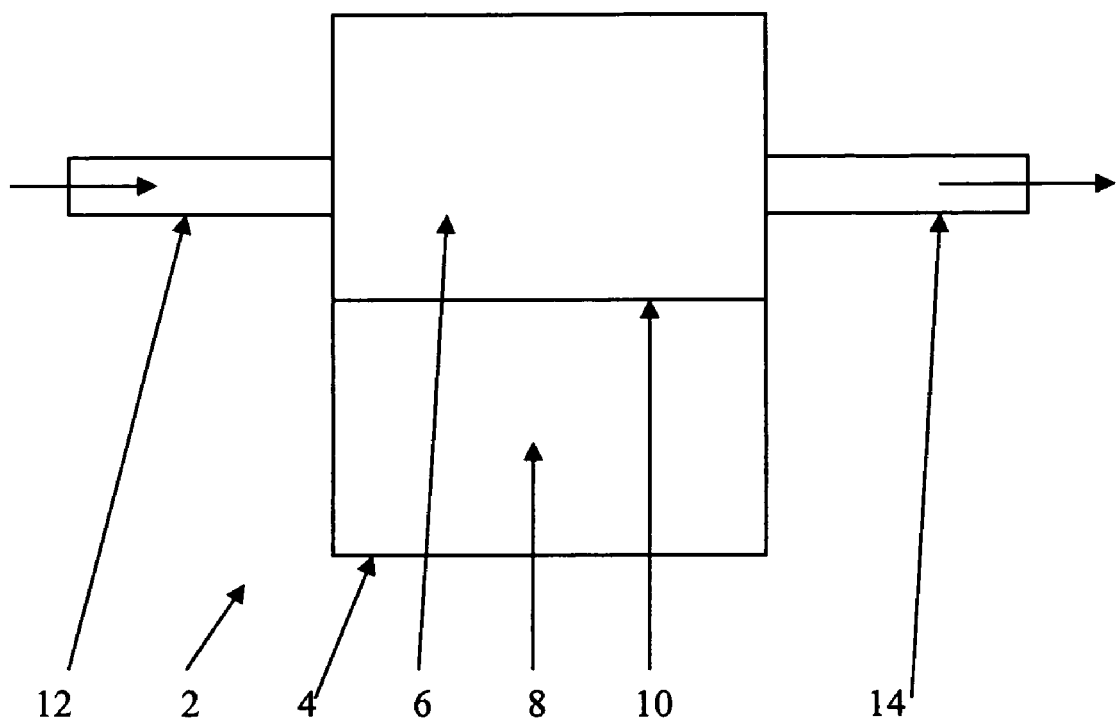
FIG. 5A illustrates a simple embodiment of the current invention.

In a preferred embodiment, there is provided a device that allows dissection and subsequent analysis of the multiple phases of HSPC homing. FIG. 5A. In its basic form, this device 2 comprises a housing 4 having a void or chamber that is separated into two compartments, an upper compartment 6 and a lower compartment 8. Alternatively, the device could comprise at least three compartments, with an upper compartment 6, at least one intermediate compartment and a lower compartment 8. The compartments 6 and 8 are separated by a membrane structure 10. Upper compartment 6 comprises an inlet 12 and an outlet 14.

Figure 5B:
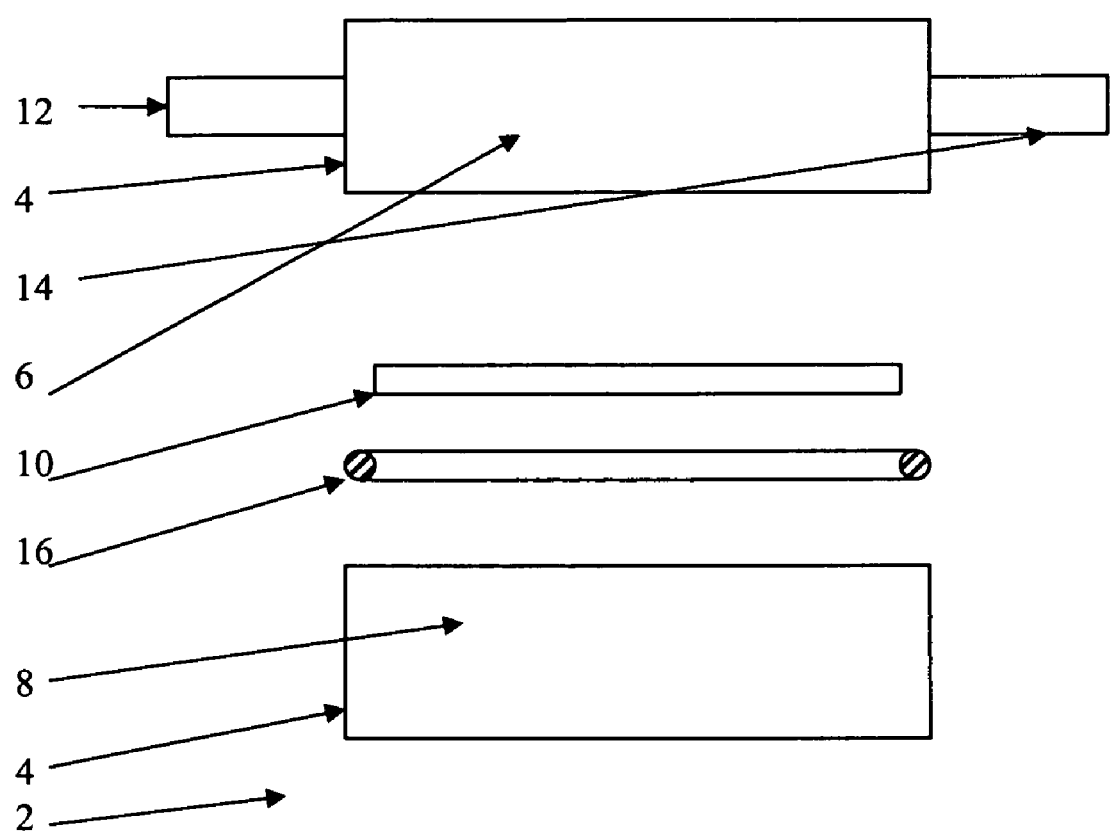
FIG. 5B is an exploded view of FIG. 5A.

It is preferable that housing 4 is comprised of a material that either has no effect on cells or has a desired effect on cells (e.g. adherence). Material that can be used with cell culture devices are well known in the art, and include, but are not limited to acrylics, borosilicates, glass, polypropylene and combinations thereof. It is further preferred that housing 4 has a first detachable segment, which is roughly equal to the area forming upper compartment 6, and a second detachable segment, roughly equal to the area forming lower compartment 8. FIG. 5B. There is a functional benefit to having housing 4 detachably segmented as such, and that benefit includes, but is not limited to removal and addition of membrane 10, removal and addition of reagents from the compartments 6 and 8 and cleaning. In the embodiment wherein housing 4 comprises detachable segments, the device further comprises a gasket 16 to facilitate an airtight seal between the detachable segments of housing 4.

Figure 6A:
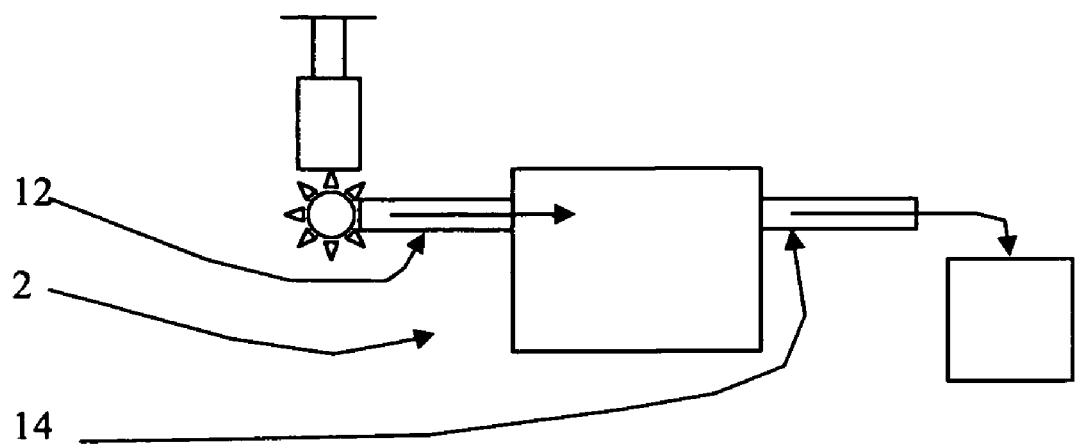
FIG. 6A illustrates one means of delivering and receiving a substance by the device chamber.

Inlet 12 is preferably dialysis tubing and is further connected to a delivery means. In the preferred embodiment, this delivery means is an automatic pump. But, the invention is not limited to an automatic pump delivery means, and can further comprise a syringe or any other delivery means known in the art. Outlet 14 is preferably dialysis tubing and is further connected to a receiving means, and that receiving means is preferably an automatic pump, but can also be a beaker, a cell culture flask or any other receiving means known in the art. FIG. 6A.

Figure 6B:
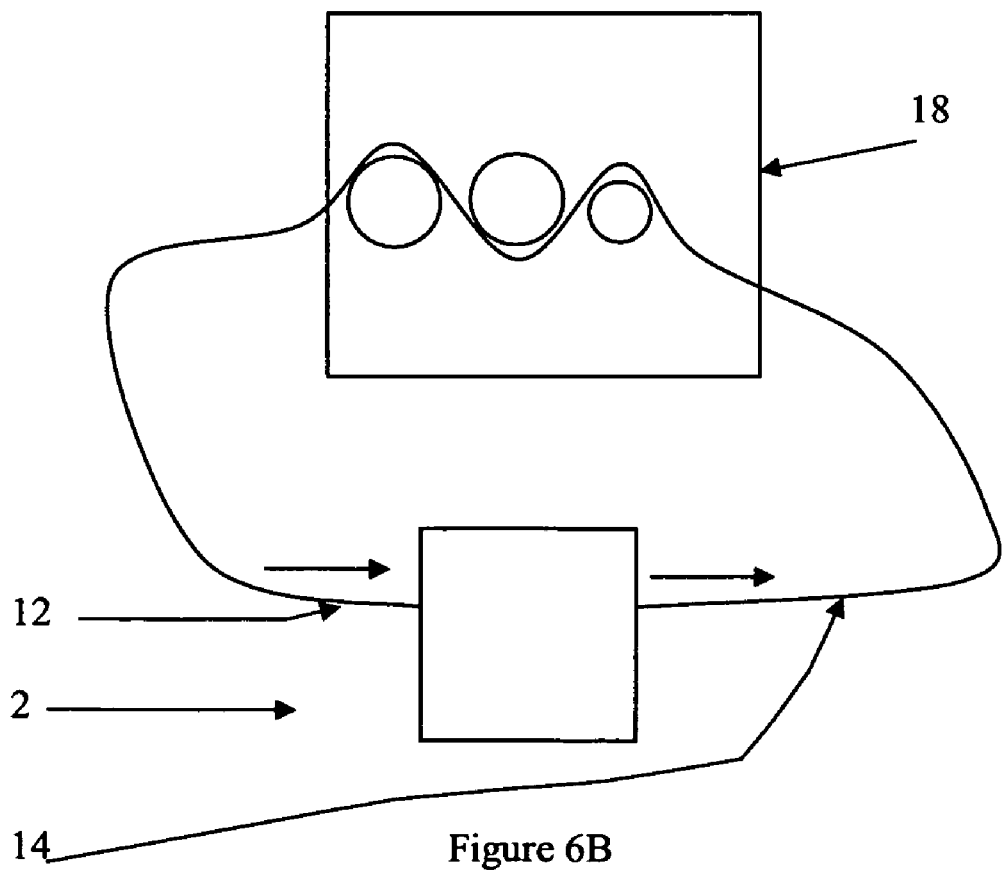
FIG. 6B illustrates another means of delivering and receiving a substance by the device chamber.

In a most preferred embodiment, inlet 12 and outlet 14 are connected to a peristaltic pump 18 which acts as both the delivery means and the receiving means, (FIG. 6B). In this embodiment, the peristaltic pump 18 will deliver a substance to inlet 12 via positive pressure, the substance will traverse the void of chamber 4 and will exit through outlet 14 where the negative pressure of the peristaltic pump 18 will draw the substance. As the substance approaches the peristaltic pump, the pressure changes from negative to positive and the substance is again delivered to the inlet 12. This preferred arrangement allows the substance to continually cycle through the housing 4 until the peristaltic pump 18 is turned off.

While the peristaltic pump 18 is a convenient means for continual cycling of a substance through housing 4, other means can be used. For example, in the set-up described for FIG. 6A, the substance can be delivered to inlet 12 using a syringe. The positive pressure of the syringe, when depressed, will cause the substance to traverse the void of housing 4 and exit into the beaker through outlet 14. To run a second cycle, the dispelled substance in the beaker can be added to the syringe and the process repeated. Other means for continual cycling of a substance through housing 4 are readily apparent to those of ordinary skill in the art.

Membrane 10 is preferably a micro-porous membrane surface made of polycarbonate (GE Osmotics, Westborough, Mass.). The membrane 10 is inserted into the void of housing 4, thereby separating upper compartment 6 from lower compartment 8. In the embodiment wherein housing 4 is detachably segmented, membrane 10 can be added and removed when housing 4 is detached. In a further embodiment, membrane 10 can be inserted into and removed from housing 4 through a slot in housing 4 (not shown). In a still further means, membrane 10 can be a fixed part of housing 4, such that housing 4 were used as a single use disposable device. In this such embodiment, housing 4 further comprises a means for extracting the substances in lower compartment 8, on membrane 10 and/or in upper compartment 6.

In an alternative embodiment, housing 4 comprises more than one membrane 10. FIG. 2. In this embodiment, a series of membranes 10 are added to the void of housing 4. The membranes 10 can have a variety of different properties, such as: (1) varied pore sizes for compartmentalizing decreasingly sized substances in lower compartment 8; (2) varied chemical make-up for sequential analysis of the effects of these varied chemicals on a substance (e.g., a series of membranes each having a covalently linked enzyme, like phosphatases and kinases, thought to play a role in a signal transduction cascade or having a variety of covalently linked soluble factors like IL-1 or IL-6 and determining the sequential effect of these factors on a substance passing through the membranes); or (3) varied coatings, such as matrigel (BD Biosciences, USA), to determine the invasive properties of a cell. In the preferred embodiment, there is provided a single membrane 10, and that membrane 10 is preferably porous, thereby allowing for the separation of substances based on size.

Figure 7A:
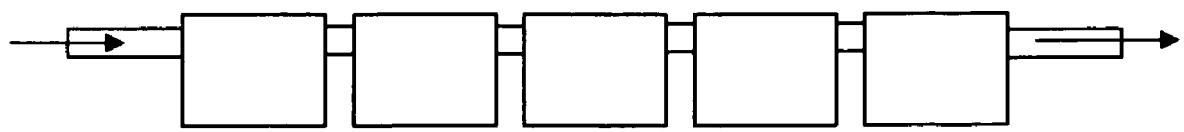
FIG. 7A illustrates a plurality of device chambers in series.
Figure 7B:
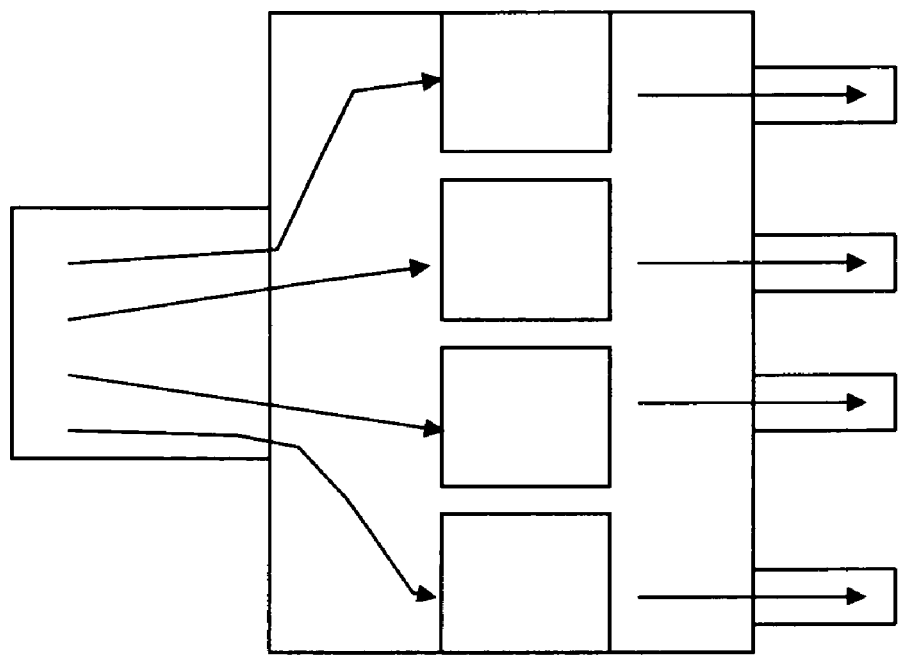
FIG. 7B illustrates a plurality of device chambers in parallel.

The device 2 has been described above comprising a single housing 4; however, this description was done for simplicity. The invention is such that the device 2 can comprise one or more housings 4, and thereby is useful in high throughput applications. Thus, device 2, when comprising more than one housing 4, can offer a variety of environments based on the membrane 10 arrangement in each housing 4. The varied housing 4 can be arranged in series or in parallel between inlet 12 and outlet 14. FIGS. 7A and 7B, respectively. The in parallel arrangement of the housing is useful for applications where the potential effect of one housing on the substance will have an unknown or detrimental effect on the substance as it would otherwise relate to a subsequent housing. One example is a high throughput screening assay, where the environment conditions of each housing 4 are being analyzed for their effect on a substance.

One preferred method of use for device 2 is detailed analysis of HSPC homing. As is discussed herein, the prior art is deficient in a variety of ways with respect to a detailed analysis of HSPC homing. The prior art deficiencies include the inability to distinguish between various phases of HSPC homing, the inability to study in vitro the phases of HSPC homing under the conditions of physiological stress, and the inability to provide a customized micro-environmental niche. Using the current invention device, these deficiencies are overcome and a detailed analysis of HSPC homing is obtained. Transmigrated cells (upper compartment 6) and non-transmigrated cells (lower compartment 8) are separately isolated and these subpopulations of HSPC examined in order to understand the difference in their gene expression that determines their functional divergence. Overall, the invention device provides a unique opportunity to dissect the complex cascade of cell homing and offers a possibility to further delineate the molecular mechanisms mediating each phase in human stem cell homing.

Figure 1B:
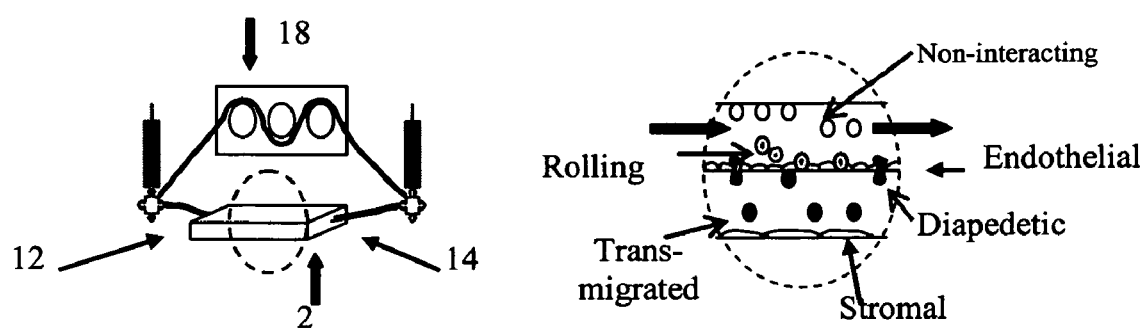
FIG. 1B illustrates the flow chamber of the current invention having the cells of the homing process separated for detailed analysis.

FIG. 1B illustrates the device of the present invention. The housing comprises a void or chamber consisting of two compartments separated by a replaceable membrane with a pore size preferably from 3.0 microns to 8.0 and most preferably 5.0 microns. The choice of pore size depends on the application of the invention device. For example, as applied to an assay for determining which phase an HSPC cell is in during the multiphase homing process, a membrane having a pore size of about 5.0 microns is preferred. For applications studying larger cells, such as tumor cells, a pore size of about 8.0 microns is preferred. Endothelial cells are grown on this membrane and the membrane is added to the chamber separating the upper compartment 6 from the lower compartment 8. Defined levels of flow (wall shear stress) are applied to the upper cell of the flow chamber by perfusing media into the inlet 12 using a constant infusion pump as the delivery means. HSPCs are injected into this perfusion circulation using a syringe connected through a cockstop. Injected cells are allowed to circulate in the flow during any given period of time.

To use the new device, glass cover slips are coated with poly-L-lysine (10.micro.g/ml) overnight at 4.deg.C. and washed twice with PBS. Primary human bone marrow derived stromal cells can be grown on these glass cover slips until 100% confluent. The cover slips are placed on the bottom of the lower compartment 8 of the flow chamber. Bone marrow derived human endothelial cells (BMEC-1, HBME-1, TrHBMEC or others) can be grown on the membrane (5.0 micron pore size) until 100% confluent. Confluence of about 100% is preferable because, as applied to HSPC homing, this confluence mimics physiological conditions. However, the confluence of cells grown on the membrane is variable depending on a variety of factors, such as physiological conditions, non-physiological conditions, phenomena being studied using the invention device and cell line, to name a few. The membrane is then placed into the flow chamber to separate the upper compartment 6 from the lower compartment 8. Defined levels of flow (wall shear stress or shear forces) are applied to the upper compartment 6 of the flow chamber (100 .micro.m thickness) by perfusing warm media (RPMI containing 0.75 mM $Ca^{2+}$ and $Mg^{2+}$ and 0.2% HSA) with a constant infusion pump (Harvard Apparatus). Purified human HSPC ($5\times10^4$ cells) are injected into the circulation and allowed to circulate for chosen period of time. Endothelial cells withstand physiological shear forces, without interrupting their continuity, for longer than 4 hours. Delivering a physiological shear force for longer periods of time (6 h, 12, or 24 h) can be pre-tested in a separate series of experiments to determine the effect of this prolonged force on the endothelial cells before injecting the HSPC. The interactions of the injected cells with the endothelial layer are observed using an inverted phase contrast microscope, and the images video-recorded. The rolling HSPC demonstrate multiple discrete interruptions and move slowly, whereas the adherent cells remain stationary at a given point for extended periods of time. Although HSPCs usually exhibit weak non-specific binding under flow conditions, the connective tubing is pre-incubated with 1% BSA. Results are expressed as the numbers of rolling or adherent cells/field (average of 4 fields) per $5\times10^4$ HSPC during an arbitrary observation period. The whole system is kept at 37.deg.C. between recordings.

Figure 2A:
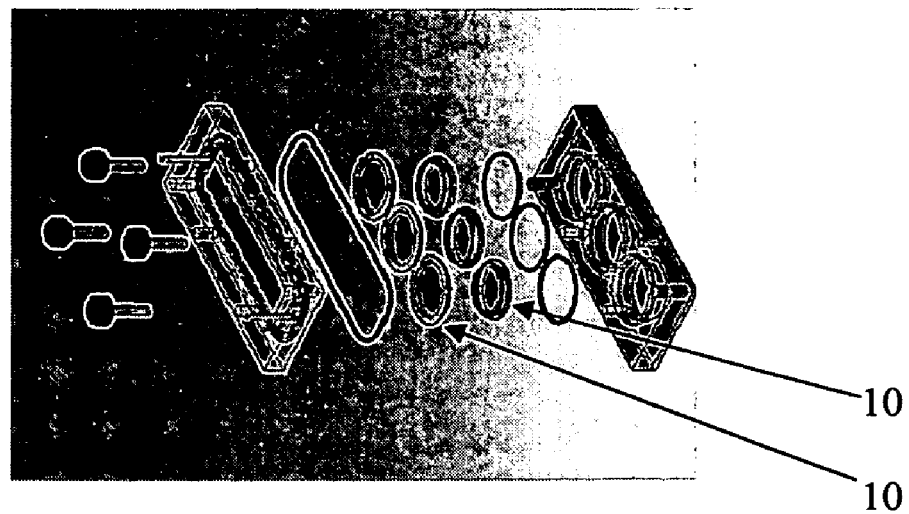
FIG. 2A is a top view and a cross section side view of one embodiment of the device of the present invention.

FIG. 2 illustrates another embodiment of the device of the present invention. In FIG. 2A, there is shown a top view drawing and a horizontal section view. In this embodiment the device comprises three chambers 4, each having an upper membrane 10 and a lower membrane 10. Endothelial cells are grown on the upper membrane 10 and matrigel is added to the lower membrane 10. Lower compartment 8 can comprise SDF-1 producing cells or other chemoattractant for drawing HSPCs to the lower chamber.

Figure 2B:
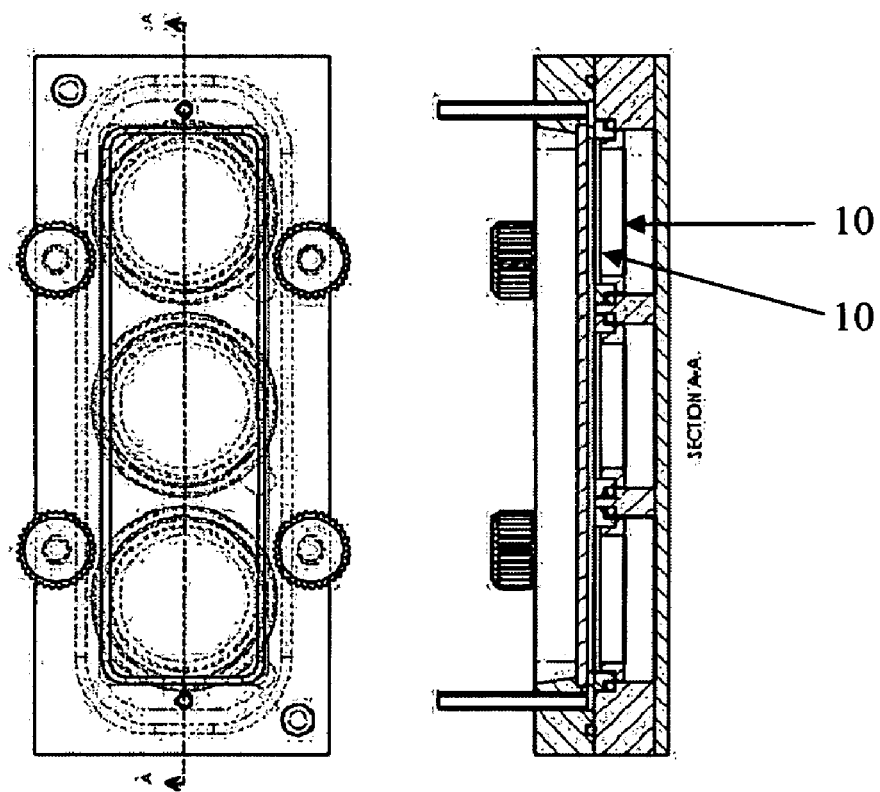
FIG. 2B is an exploded view of one embodiment of the device of the present invention.

FIG. 2B is a blown apart isometric view illustrating the integral parts of this embodiment of the device 2: four screws, an acrylic top block with a borosilicate glass window, upper chamber seal, upper membrane 10 and lower membrane 10, the lower o-ring and the three chamber 4 acrylic bottom block.

FIGS. 3A and 3B are photographs of the two-cell parallel flow chamber connected to a peristaltic pump. 3A: The flow chamber was assembled under sterile conditions in a cell culture hood. The peripheral blood cells were drawn in by suction. 3B: The flow chamber device and the peristaltic pump were then transferred in the cell culture incubator. The peripheral blood cells depleted from erythrocytes were allowed to circulate through the chamber for 4 hours. The chamber was then disassembled in the cell culture hood.

As used in this first preferred method, the device 2 comprises three chambers 4 arranged in series between the inlet 12 and the outlet 14. Various bone marrow derived human stromal cell lines that differ in their ability to produce chemoattractants, including SDF-1, can be grown on a cover slip and placed on the bottom of the lower compartment 8 in the flow chamber 4. Alternatively, SDF-1 (10 ng/ml) can be added to the lower compartment 8 of the flow chamber instead of stromal cells as a positive control. SDF-1-specific neutralizing antibodies will be used to verify SDF-1-dependent transmigration of HSPC from the upper compartment 6 into the lower compartment 8 of the flow chamber 4. After a chosen period of time the chamber 4 is disassembled, transmigrated cells are collected and are examined using clonogenic assays (CFU and LTC-IC) and FACS. The stromal cell line that induces the highest migratory activity of HSPC under conditions of shear stress can be characterized.

The sample substance to be perfused through the chambers 4 is HSPC purified from whole blood. A pool of stem and progenitor cells purified from a donor's blood or bone marrow is heterogeneous. In addition to hematopoietic progenitor cells at different levels of differentiation, it consists of hematopoietic stem cells of long-term and short-term repopulation potential, as well as mesenchymal stem cells, endothelial precursors and other adult stem cells. From a clinical point of view it is crucial to understand the cellular and molecular mechanisms that mediate homing of each subpopulation of stem cells. The invention device allows for various microenvironmental niches to be created and further to isolate cells that will preferentially migrate toward those niches. Isolated cells can be assayed using multiple techniques, including in vivo and in vitro assays. Preferential migration of stem cells toward different microenvironments, including organ specific microenvironments, might provide an important insight in understanding organ specific homing of transplanted cells.

After 2, 4, 6, 12 or 24 hours of circulation, the cells that have not adhered to the endothelial monolayer will be washed out and collected. Then the chamber can be disassembled, the membrane separating the lower compartment 8 from the upper compartment 6 of the chamber with the monolayer of endothelial cells will be carefully removed from the chamber and placed in a trypsin solution to prepare a single cell suspension. Along with endothelial cells, the suspension will contain adherent but not transmigrated HSPC. Finally, HSPC suspended in the lower compartment 8 of the flow chamber and HSPC adherent to the stromal monolayer can be harvested. Three subpopulations of HSPC, ((1) HSPC that fail to adhere to endothelial cells; (2) HSPC arrested on the endothelial monolayer; and (3) transmigrated cells) can be collected and examined by CFU, LTC-IC assays and FACS analysis.

There is growing evidence of the importance of wall shear stress in the regulation of endothelial cell functions (reviewed in Nerem R M (1991) ASGSB Bull 4(2):87-94; Topper J N, Gimbrone Mass. (1999) Mol Med Today 5(1):40-46.; Nerem R M et al (1998) Am J Med Sci 16(3):169-175). It has been demonstrated that shear forces induce rapid cytoskeletal remodeling, activation of signaling cascades and transcription factors, and differential gene expression (reviewed in Ballerman B J, et al (1998) Kidney Int Suppl 67:S100-108.; Barakat A I. (1999) Int J Mol Med 4(4):323-332; Shyy J Y. (2001) Biorheology 38(2-3):109-117). The device of the current invention produces the shear forces to induce these changes to the endothelial cells, thereby allowing for analysis of the mechanisms involved in the regulating HSPC rolling on, adhesion to, and transmigration across endothelium cells under the conditions of physiological flow. The chamber design further allows antibodies or soluble factors of interest to be injected directly into the flow during the experiment. Long-term or short-term exposure to various chemoattractants, cytokines, defensins, membrane phospholipids or chemokines, such as IL-1, IL6, Leukotrine B.sub.4, RANTES, CCR5, TNF-a, MIP-1a and TGF-.beta. etc, creates a unique micro environment, and can be customized to model inflammatory response, degeneration or any other pathophysiological conditions. These studies also provide a significant contribution to the clinic-related research of directed stem cell homing into areas of inflammation or drug-induced damage. Other microenvironmental niches are useful with the current device and methods.

The rapid effect that shear force induces on endothelial cells might itself create an "inflammatory-like" environment. Endothelial cells adapt to sustained shear stress (reviewed in Ballerman B J, et al (1998) Kidney Int Suppl 67:S100-108.; Fisher A B, et al (2001) Am J Physiol Lung Cell Mol Physiol 281(3):L529-533), therefore, endothelial monolayers can be assembled in the flow chamber and incubated at 37.deg.C. for 12 hours under the conditions of shear stress before the experiment. The adapted endothelial cells might represent natural bone marrow sinusoids. If needed, various media will be tested to optimize endothelial cell survival under conditions of flow.

Another benefit of the newly designed flow chamber is the possibility to utilize various stromal cell lines as a source of chemoattractants. It has been shown before that the stromal microenvironment might affect the function of endothelial cells (Bautz F, et al (2000) Exp Hematol 28(6):700-706; Rainger GE, et al (2001) Immunol Methods 255(1-2):73-82). Therefore, the new device allows us to combine the effect of shear stress and the effect of stromal microenvironment on endothelial cell functions to study HSPC and endothelial cell interactions in vitro. The design of the entire system allows several flow chambers to be assembled in one series chain, so that competitive homing of HSPC can be studied. Use of stromal cells isolated from different organs might be useful to study "organ specific homing" of stem cells. This approach might help us understand the recently discovered phenomenon of lodging of stem cells isolated from bone marrow or blood, into organs other than the bone marrow. Also, the use of stromal and endothelial cell lines is beneficial because it offers an opportunity to manipulate the expression of a gene of interest in order to determine its role in HSPC homing. Additionally, other cells of the hematopoietic microenvironment, in addition to stromal cells, might have a crucial effect on endothelial cell function. Therefore, an adherent layer of primary bone marrow cultures (e.g., long term bone marrow culture, or LTBMC) can be used instead of the stromal monolayer. Prior to use, the LTBMC will be irradiated to abrogate endogenous hematopoiesis and to more closely approximate the in vivo clinical situations. Similarly, endothelial and stromal cells can be irradiated prior to their use, bringing the experimental conditions in vitro closer to those used in vivo and in clinical situations.

Figure 4A:
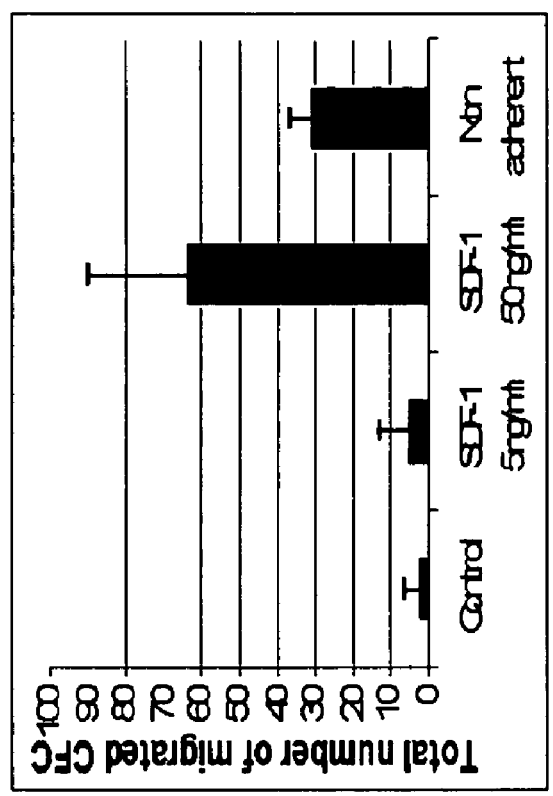
FIG. 4 depicts the results of experiments designed to test the ability of the device to support HSPC homing under conditions of shear stress in vitro.
Figure 4B:
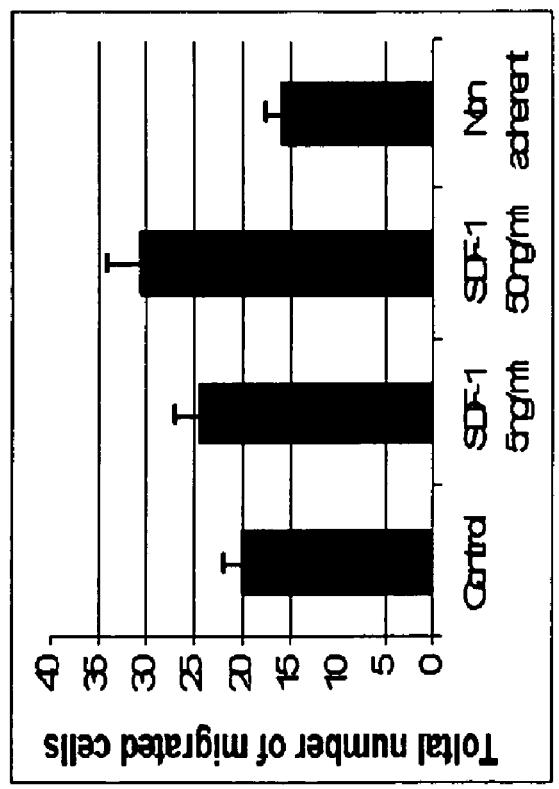

FIG. 4 demonstrates SDF-1 transmigration of HSPC under conditions of physiological shear stress. Human peripheral blood cells were allowed to circulate in the flow chamber for 4 hours. Transmigrated cells were collected and enumerated (A). The number of colony forming cells (CFC) was assayed using methylcellulose assay. Data are expressed as mean+/−SD. The experiment was designed as follows: All parts of the device were sterilized using 70% ethanol. The upper membranes were then pre-coated with 0.2% gelatin for 5 minutes at room temperature. The human endothelial cells were then grown on the membrane. TrHBMEC human bone marrow derived cell lines were used in all experiments. The dynamic of cell growth was monitored under the inverted microscope. When endothelial cells were 100% confluent, the inserts were transported into the wells of the bottom block. Prior to that, the wells were filled either with the plain culture media, or with the media supplemented with SDF-1. The top block was connected to the bottom block by screws, and attached to the sterile catheter tubing, which were extended through the peristaltic pump. Thereafter, by using the negative pressure created by the peristaltic pump, the chamber was filled by placing the inlet catheter in the 15 ml tube with the culture media. Freshly harvested peripheral blood cells were purchased from San Diego Blood Bank on the day of the experiment. The cells were depleted from erythrocytes using ammonium chloride. Prior to the flow experiment, $5 \times 10^5$ cells were aliquoted and used in the methylcellulose culture assay to monitor the number of HSPC in the initial cell suspension. The remaining cells (total of $3.5 \times 10^6$) were re-suspended in 1 ml of culture media and drawn into the chamber by suction. Thereafter, the inlet was connected to the outlet catheter, and the shear stress was applied by using a regulatory switch on the pump. The chamber and the pump were then placed in the cell culture incubator and the circulating blood cells were allowed to interact with endothelial monolayer for 4 hours at 37.deg.C. Four hours later, the cells remaining in circulation were collected through the outlet, the chamber was then disassembled, and the inserts were removed. The transmigrated cells were harvested from each well and assayed in methylcellulose cultures for the presence of HSPC (FIG. 4). As we expected, the experiment demonstrated that SDF-1 stimulated the transendothelial migration of HSPC under the conditions of shear stress in a dose-dependent manner.

Figure 8A:
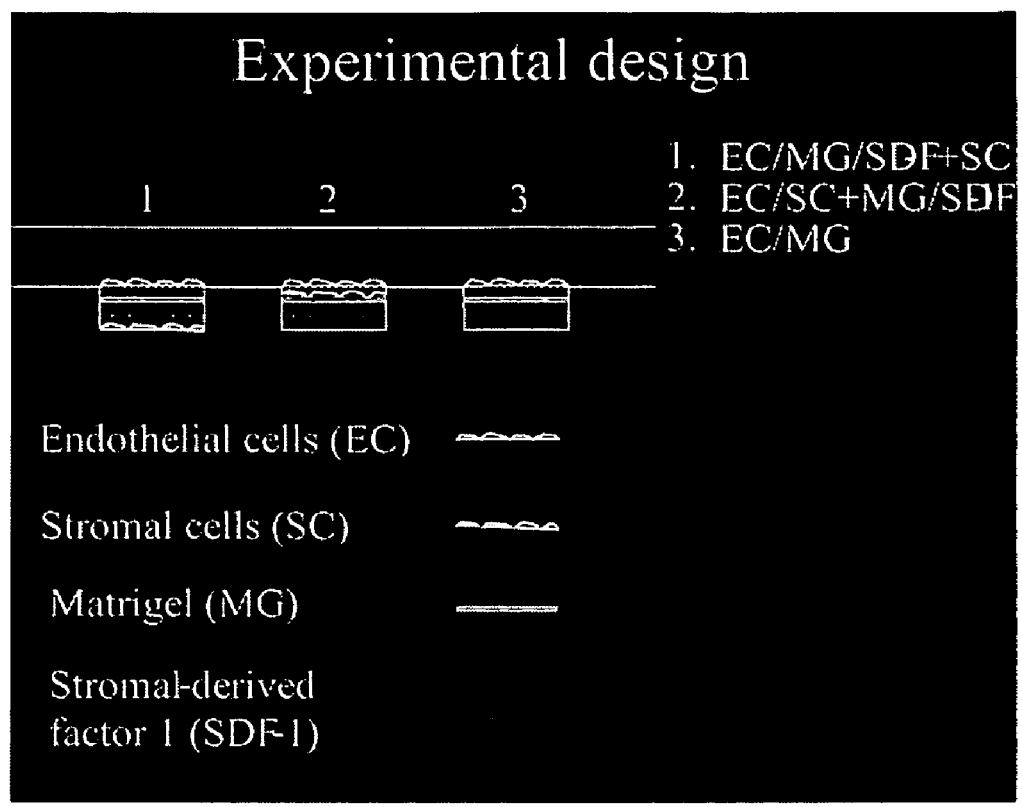
FIG. 8A illustrates the experimental design of stromal cells facilitating SDF-1-mediated transendothelial migration of bone marrow cells and chamber assembly.
Figure 8B:
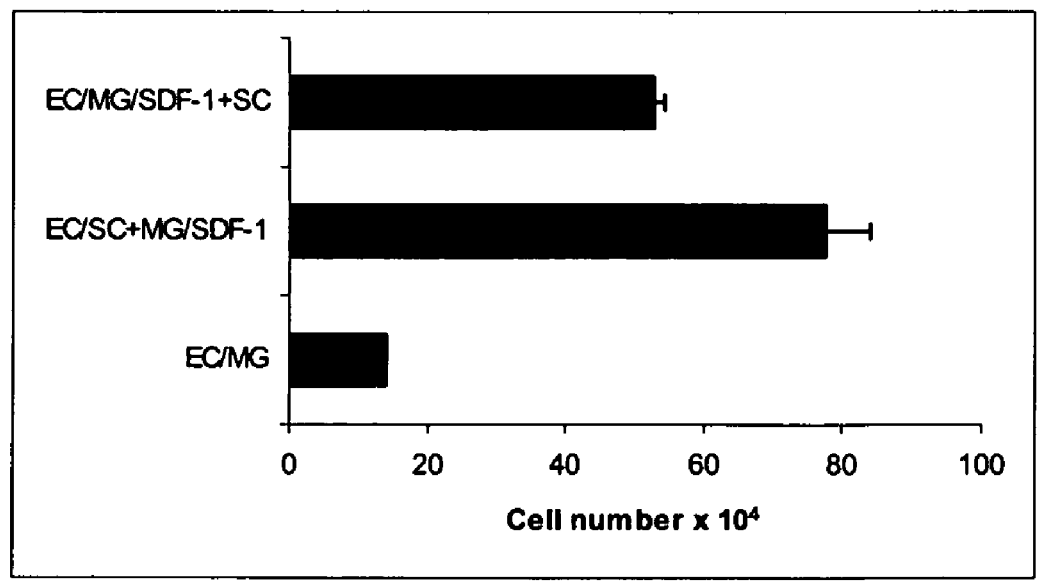
FIG. 8B illustrates the experimental results obtained from the assembly illustrated in FIG. 8A.

FIG. 8 depicts stromal cells facilitating SDF-1-mediated transendothelial migration of bone marrow cells. The experimental design and chamber assembly is illustrated in FIG. 8A. The assembly consisted of: endothelial cells/matrigel/stromal-derived factor 1+stromal cells (well #1); endothelial cells/stromal cells+matrigel/stromal-derived factor 1 (well #2); and endothelial cells/matrigel (well #3). Bone marrow cells were injected into the flow chamber and were allowed to transmigrate under shear stress conditions for 4 hours. The chamber was then disassembled, the transmigrated cells were collected and the results were calculated. FIG. 8B describes the experimental results obtained from this assembly. It was demonstrated that transmigration of bone marrow cells is increased if stromal cells are in close proximity to endothelial cells. FIG. 8B, well #2. This finding suggests the existence of cross-talk between endothelial cells and stromal cells that might be important for extravasation of the migrating cells.

A method for studying the migration of a variety of cells using the invention device wherein the cells comprise stem cells, malignant cells and mature cells is described herein. The mature cells comprise eosinophils, lymphocytes, platelets and neutrophils. The device is configured to study the migration of the variety of cells, for example, having a membrane with pore sizes ranging from 3.0 microns to 8.0 microns. The device is configured to provide a suitable microenvironmental niche for the cell type and the goals of the study. For example, the microenvironmental niche is configured to study organ specific migration, and as such is an organ specific microenvironmental niche and the membrane is configured to study organ specific migration. Also the membrane is configured to support growth of a cell. Additionally, the microenvironmental niche is configured to model a disease state; the microenvironmental niche is configured to model a disease state in the presence of a treatment drug; and the microenvironmental niche is configured to screen for treatment drugs that do not have a detrimental effect on the cell function.

Various modifications and alterations of the invention will become apparent to those skilled in the art without departing from the spirit and scope of the invention, which is defined by the accompanying claims. For example, it should be noted that steps recited in any method claims do not necessarily need to be performed in the order that they are recited. Those of ordinary skill in the art will recognize variations in performing the steps from the order in which they are recited. For example, in certain embodiments, steps may be performed simultaneously. The accompanying claims should be construed with these principles in mind.

I claim:

1. A device for evaluating the process of a multi-phased biological event the device comprising:
   (a) at least one housing, wherein each housing is capable of characterization, analysis and manipulation independent of any other housing and wherein the housing further comprises:
      (i) a chamber;
      (ii) an inlet connected to the chamber for delivering a substance into the chamber;
      (iii) an outlet connected to the chamber for removing the substance from the chamber;
      (iv) at least one porous membrane, wherein the membrane is situated within the chamber of the housing such that at least two compartments are created by the relation of membrane surfaces with the chamber wherein the housing disassembles into a top segment, thereby forming an upper compartment defined as being the top segment and the membrane, and into a bottom segment, thereby forming a lower compartment defined as being the remainder of the housing and the substance flows in a manner parallel to the membrane only in the upper compartment above the membrane such that flow perpendicular to the membrane is avoided;
   (b) a delivery means; and
   (c) a receiving means, wherein a substance is delivered into the chamber of the housing via the inlet and constituents of the substance engage in various phases of a multi-phase biologic process.

2. The device of claim 1 wherein the housing is made of a material that is suitable for the substance that passes through the housing.

3. The device of claim 2 wherein the housing is made of a material comprising acrylic, borosilicate, glass, polypropylene and combinations thereof.

4. The device of claim 3 where the housing is borosilicate.

5. The device of claim 1 wherein the membrane is inserted in the void of the housing chamber such that an independent upper compartment and an independent lower compartment are formed.

6. The device of claim 1 wherein more than one membrane is inserted into the void of the housing chamber forming an independent upper compartment, at least one independent intermediate compartment, and an independent lower compartment.

7. The device of claim 1 wherein more than one membrane is inserted into the void of the housing chamber forming an independent upper compartment and an independent lower compartment having multiple membranes, wherein the upper compartment and lower compartment are further divided into independent sub-compartments.

8. The device of claim 1 wherein the housing can be disassembled into multiple segments.

9. The device of claim 8 wherein the housing can be disassembled into a top segment and a bottom segment.

10. The device of claim 9 wherein the housing is disassembled into a top segment and bottom segment at the insertion point of the membrane, thereby separating the compartments.

11. The device of claim 1 wherein the inlet and outlet are attached to the housing so that the substance is delivered to the upper compartment.

12. The device of claim 1 wherein the inlet and the outlet attached to the top segment housing at a location so that the inlet and outlet are at distal ends of the membrane.

13. The device of claim 12 wherein the top segment and the bottom segment are attached to form a unified unit.

14. The device of claim 1 wherein the delivery means is not limited to a pump and comprises a syringe, a pump, a vacuum, a pressurized gas container and a peristaltic pump.

15. The device of claim 1 wherein the receiving means is not limited to a pump and comprises a syringe, a pump, a vacuum, a pressurized gas container and a peristaltic pump.

16. The device of claim 1 wherein the delivery means and the receiving means are the same means.

17. The device of claim 16 wherein the means is a peristaltic pump.

18. The device of claim 17 wherein the means is a single peristaltic pump and the inlet and outlet are connected to the peristaltic pump by a single dialysis tubing, thereby providing a continuing in and out cycling of the substance through the chamber.

19. The device of claim 1 wherein the pores are between 3.0 microns and 8.0 microns.

20. The device of claim 1 wherein the pores are 5.0 microns.

21. The device of claim 1 wherein the membrane supports the attached cell growth.

22. The device of claim 1 wherein, if more than one housing is utilized for the device, the more than one housing is connected in parallel.

23. The device of claim 1 wherein, if more than one housing is utilized for the device, the housing is connected in series.

24. The device of claim 1 wherein the device is useful for high throughput applications.

* * * * *